(12) United States Patent
Zhu et al.

(10) Patent No.: US 10,562,895 B2
(45) Date of Patent: Feb. 18, 2020

(54) PYRROLOQUINOLINE QUINONE B CRYSTAL FORM AND PREPARATION METHOD THEREFOR

(71) Applicant: ZHUCHENG HAOTIAN PHARM CO., LTD, Weifang, Shandong (CN)

(72) Inventors: Liping Zhu, Shandong (CN); Xuefeng Mei, Shanghai (CN); Jianrong Wang, Shanghai (CN)

(73) Assignee: ZHUCHENG HAOTIAN PHARM CO., LTD., Weifang, Shandong (CN)

( * ) Notice: Subject to any disclaimer, the term of this patent is extended or adjusted under 35 U.S.C. 154(b) by 0 days.

(21) Appl. No.: 15/772,946

(22) PCT Filed: Sep. 28, 2016

(86) PCT No.: PCT/CN2016/100658
§ 371 (c)(1),
(2) Date: May 2, 2018

(87) PCT Pub. No.: WO2017/076138
PCT Pub. Date: May 11, 2017

(65) Prior Publication Data
US 2018/0319792 A1    Nov. 8, 2018

(30) Foreign Application Priority Data
Nov. 2, 2015 (CN) .......................... 2015 1 0734349

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .......................... C07D 471/84; C07B 2200/13
USPC .......................................................... 546/84
See application file for complete search history.

(56) References Cited

U.S. PATENT DOCUMENTS

2017/0022200 A1*    1/2017   Govinda .............. C07D 471/04

FOREIGN PATENT DOCUMENTS

| WO | 2011007633 A1 | 1/2011 |
| WO | 2011055796 A1 | 5/2011 |
| WO | 2015159236 A1 | 10/2015 |

* cited by examiner

*Primary Examiner* — Rita J Desai
(74) *Attorney, Agent, or Firm* — Novik, Kim & Lee, PLLC; Bin Lu

(57) ABSTRACT

The present invention relates to the technical field of chemical drugs and crystal form processes, and to a pyrroloquinoline quinine B crystal form and a preparation method therefor. The present invention comprehensively characterizes the pyrroloquinoline quinine B crystal form by virtue of means such as X-ray powder diffraction analysis, thermogravimetric analysis, and differential scanning calorimetry analysis so as to find the fact that the pyrroloquinoline quinine B crystal form is high in crystallinity and low in hygroscopicity, and a regular crystal form can be formed, thereby facilitating process treatment and improvement of physical and chemical properties of a medicine, and improving the patent medicine performance. The preparation method for the pyrroloquinoline quinone B crystal form provided in the present invention is simple, easy to control, and high in reproducibility.

13 Claims, 3 Drawing Sheets

PYRROLOQUINOLINE QUINONE B CRYSTAL FORM AND PREPARATION METHOD THEREFOR

TECHNICAL FIELD

The invention belongs to the technical field of chemical drugs and crystal technology, and in particular, relates to pyrroloquinoline quinone B crystal form and preparation method therefor.

BACKGROUND

Polymorphism refers to such a phenomenon that a solid substance in two or more different spatial arrangements forms solid states with different physicochemical properties. In the field of drug research, polymorphs also include multi-component crystal forms of such as organic solvates and hydrates.

The phenomenon of drug polymorphism is widespread in the drug development process and is an inherent characteristic of organic small molecule compounds. In theory, small molecule drugs can have an infinite number of crystal packing modes—polymorphism. Studies have shown that the number of discovered polymorphs of a drug is directly proportional to the time and resources invested in research. For example, Lipitor, the drug with the highest sales in the world, has as many as 35 patented crystal forms.

The polymorphism phenomenon is not only controlled by the intrinsic factors such as the spatial structure and functional group properties of the molecule itself, intramolecular and intermolecular interactions, but also affected by various factors such as drug synthesis process design, crystallization and purification conditions, selection of formulation excipient, process route of formulation and granulating method, storage conditions, and packaging materials. Different crystal forms have different colors, melting points, dissolution performance, chemical stability, reactivity, mechanical stability, etc. These physical and chemical properties or processability sometimes directly affect the safety and effective performance of drugs. Therefore, the research and control of crystal form has become an important research content in the drug development process.

Researches of crystal forms include two stages, discovery of crystal forms and optimization of crystal forms. In the stage of discovering crystal forms, various crystallization methods are mainly used, such as melt crystallization, solution evaporation, rapid cooling, and suspension method, by changing the external factors that affect the crystallization of drugs, such as crystallization conditions, solvent, temperature, speed and proportion of suspended solvents, etc. A high-throughput sample preparation platform is used to process hundreds of crystallization experiments simultaneously, and new crystal forms are prepared and discovered using microsample preparation technology and analytical testing methods. In the stage of optimizing crystal forms, new crystal craft is subjected to amplification and the preparation conditions are to be explored. Various solid characterization methods such as X-ray diffraction, solid-state nuclear magnetic resonance, raman spectroscopy, and infrared spectroscopy are used to characterize the crystal form. In addition, DSC, TGB, DVS, and HPLC, etc. are used to study the physicochemical properties of the crystal forms and compare the hygroscopicity, chemical stability, physical state stability, and processability of different crystal forms. Finally, the most preferred solid form is chosen for the development.

The chemical name of pyrroloquinoline quinine (PQQ) is: 4,5-Dihydro-4,5-dioxo-1H-pyrrolo[2,3-f]quinoline-2,7,9-tricarboxylic acid, and its chemical structural formula is shown as follows:

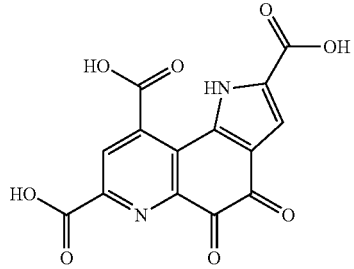 [SMILES: O=C(O)c1cc(C(=O)O)c2c(n1)C(=O)C(=O)c1cc(C(=O)O)[nH]c1-2]

PQQ is a newly discovered vitamin B, which is a coenzyme different from the oxidoreductases of pyridine nucleotides and riboflavin. The unique structure of the ortho-quinones makes PQQ unique in its physical and chemical properties and a variety of physiological functions. There is a wide application prospect in food, medicine, agriculture and other industries. PQQ has a polymorphism phenomenon; however, there are no reports of its polymorphism in patent.

A new crystal form of PQQ: crystal form B, is reported in the present invention on the basis of the comprehensive adoption of a new crystallizing nucleation methods and crystallizing conditions.

SUMMARY OF INVENTION

One of the objects of the present invention is to provide a crystal form B of pyrroloquinoline quinone having high crystallinity, low hygroscopicity, and capable of forming a regular crystal morphology.

In the first aspect of the present invention, a crystal form B of pyrroloquinoline quinone is provided, and the crystal form B of pyrroloquinoline quinone has 3 or more characteristic diffraction peaks selected from the following group consisting of: 11.10±0.2°, 17.32±0.2°, 19.40±0.2°, 20.16±0.2°, 20.53±0.2°, 22.57±0.2°, 26.14±0.2°, 29.95±0.2°, and 32.06±0.2°.

In another preferred embodiment, the crystal form B of pyrroloquinoline quinone has 3 or more characteristic diffraction peaks selected from the following group consisting of: 11.10, 15.69, 16.52, 17.32, 18.64, 19.40, 20.16, 20.53, 21.77, 22.57, 24.05, 24.36, 25.42, 26.14, 27.05, 27.60, 28.15, 29.37, 29.95, 32.06, 33.96, 35.62, 36.97, and 38.09±0.2°.

In another preferred embodiment, the X-ray powder diffraction pattern of crystal form B of pyrroloquinoline quinone is essentially as shown in FIG. 1.

In another preferred embodiment, the thermogravimetric analysis pattern of the crystal form B of pyrroloquinoline quinone has a decomposition temperature at 260° C.

In another preferred embodiment, the crystal form B of pyrroloquinoline quinone is an anhydrous crystal form.

In another preferred embodiment, the thermogravimetric analysis pattern of the crystal form B of pyrroloquinoline quinone is essentially as shown in FIG. 2.

In another preferred embodiment, the differential scanning calorimetry pattern of the crystal form B of pyrroloquinoline quinone is essentially as shown in FIG. 3.

In another preferred embodiment, the infrared spectrum of the crystal form B has characteristic peaks at least at 3344 cm$^{-1}$, 3257 cm$^{-1}$, 2808 cm$^{-1}$, 2596 cm$^{-1}$, 1745 cm$^{-1}$, 1726 cm$^{-1}$, 1710 cm$^{-1}$, 1691 cm$^{-1}$, 1643 cm$^{-1}$, 1508 cm$^{-1}$, 1402 cm$^{-1}$, 1336 cm$^{-1}$, 1261 cm$^{-1}$, 1207 cm$^{-1}$, 1080 cm$^{-1}$, and 769 cm$^{-1}$.

In another preferred embodiment, the infrared spectrum of the crystal form B of pyrroloquinoline quinone is essentially as shown in FIG. 4.

In another preferred embodiment, the hygroscopicity analysis of the crystal form B shows that one molecule of water at a relative humidity of 85-95% is adsorbed to form a monohydrate.

In the second aspect of the present invention, a preparation method for a crystal form B of pyrroloquinoline quinone is provided, which is simple to operate and has a good reproducibility.

The preparation method comprises the following steps: pyrroquinoline quinine acid (PQQ acid) is placed in a vacuum drying oven at room temperature, and the temperature is raised, and the crystal form B of pyrroloquinoline quinone is obtained, wherein, the pyrroquinoline quinine acid refers to 4,5-dioxy-4,5-dihydro-1H-pyrrole [2,3-f] quinoline-2,7,9-tricarboxylic acid.

In another preferred embodiment, the temperature is raised to 130-160° C., preferably 140-150° C.

In another preferred embodiment, the time is kept for 3-5 hours after the temperature is raised.

Due to the adoption of the above technical solution, the beneficial effects of the present invention are:

The crystal form B of pyrroloquinoline quinone provided by the present invention has a high crystallinity and a low hygroscopicity, and can form a regular crystal morphology, which is beneficial to the technology processing of drugs and the improvement of physicochemical properties, and can improve the druggability; and the preparation method has the advantages of simple processing, easy operation, and good reproducibility.

DETAILED DESCRIPTION

Figure 1:
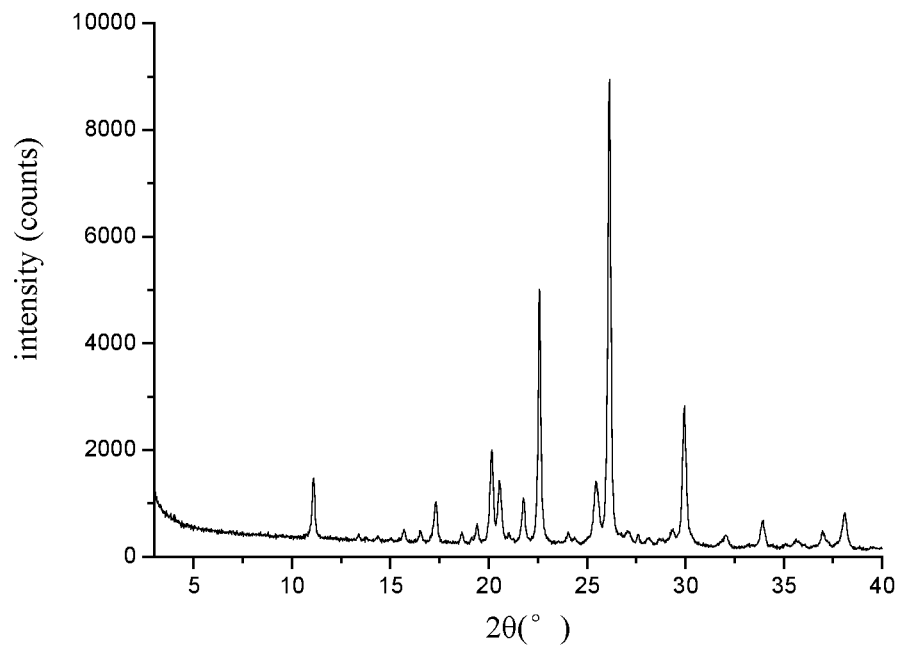
FIG. 1 is an X-ray powder diffraction (XRPD) pattern of the PQQ crystal form B provided in Example 1.

In order to make the objectives, technical solutions and advantages of the present invention more obvious, the present invention is further described in detail below with reference to the figures and embodiments. It should be understood that the specific embodiments described herein are only used to explain the present invention, and not intended to limit the present invention.

Example 1

20.0 mg of PQQ acid was placed in a glass bottle. The open glass bottle was placed in a vacuum drying oven and heated to 140° C. for 5 h to give a 20.00 mg of crystal form B of pyrroloquinoline quinone with a yield of 100%. The crystal form B of pyrroloquinoline quinone is a red crystalline powder.

Example 2

20.0 mg of PQQ acid was placed in a glass bottle. The open glass bottle was placed in a vacuum drying oven and heated to 140° C. for 6 h to give a 20.00 mg of crystal form B of pyrroloquinoline quinone with a yield of 100%. The crystal form B of pyrroloquinoline quinone is a red crystalline powder.

Example 3

20.0 mg of PQQ acid was placed in a glass bottle. The open glass bottle was placed in a vacuum drying oven and heated to 140° C. for 5.5 h to give a 20.00 mg of crystal form B of pyrroloquinoline quinone with a yield of 100%. The crystal form B of pyrroloquinoline quinone is a red crystalline powder.

Example 4

20.0 mg of PQQ acid was placed in a glass bottle. The open glass bottle was placed in a vacuum drying oven and heated to 150° C. for 4.5 h to give a 20.00 mg of crystal form B of pyrroloquinoline quinone with a yield of 100%. The crystal form B of pyrroloquinoline quinone is a red crystalline powder.

Example 5

20.0 mg of PQQ acid was placed in a glass bottle. The open glass bottle was placed in a vacuum drying oven and heated to 150° C. for 5 h to give a 20.00 mg of crystal form B of pyrroloquinoline quinone with a yield of 100%. The crystal form B of pyrroloquinoline quinone is a red crystalline powder.

Example 6

20.0 mg of PQQ acid was placed in a glass bottle. The open glass bottle was placed in a vacuum drying oven and heated to 150° C. for 6 h to give a 20.00 mg of crystal form B of pyrroloquinoline quinone with a yield of 100%. The crystal form B of pyrroloquinoline quinone is a red crystalline powder.

The crystal form B of pyrroloquinoline quinone provided by the present invention is characterized by solid-state methods, such as an X-ray powder diffraction (XRPD), a thermogravimetric analysis (TG), a differential scanning calorimetry analysis (DSC), an infrared (IR) analysis, and a hygroscopicity analysis (DVS).

A solid sample of the crystal form B of pyrroloquinoline quinone obtained in Example 1 was subjected to the X-ray powder diffraction analysis using a Bruker D8 BdvBnce-type diffractometer from Brook Instrument Co., Ltd., Germany, using a Cu-K ray ($\lambda$=1.5418 Å) with a voltage of 40 kV, a current of 40 mA, a step size of 0.02 degrees, and 0.1 second for each step. The analysis results were shown in FIG. 1.

A solid sample of the crystal form B of pyrroloquinoline quinone obtained in Example 1 was subjected to the thermogravimetric analysis, using a TG20F3 type thermogravimetric analyzer from Naichi Scientific Instruments Co., Ltd., Germany, with an atmosphere was nitrogen and the heating rate was 10 degrees/minute. The analysis results were shown in FIG. 2.

A solid sample of the crystal form B of pyrroloquinoline quinone obtained in Example 1 was subjected to the differential scanning calorimetry analysis, using a DSC 8500 differential calorimeter from Perkin Elmer Corporation of the United States, with an atmosphere of nitrogen and a heating rate of 10 degrees/minute. The analysis results were shown in FIG. 3.

A solid sample of the crystal form B of pyrroloquinoline quinone obtained in Example 1 was subjected to an infrared spectrum analysis at room temperature using a Nicolet-MBgnB FT-IR 750 infrared spectrum analyzer from Nicoloi Corporation of the United States, with a detection range of 4000-350 $cm^{-1}$ wavenumber. The analysis results were shown in FIG. 4.

Figure 5:
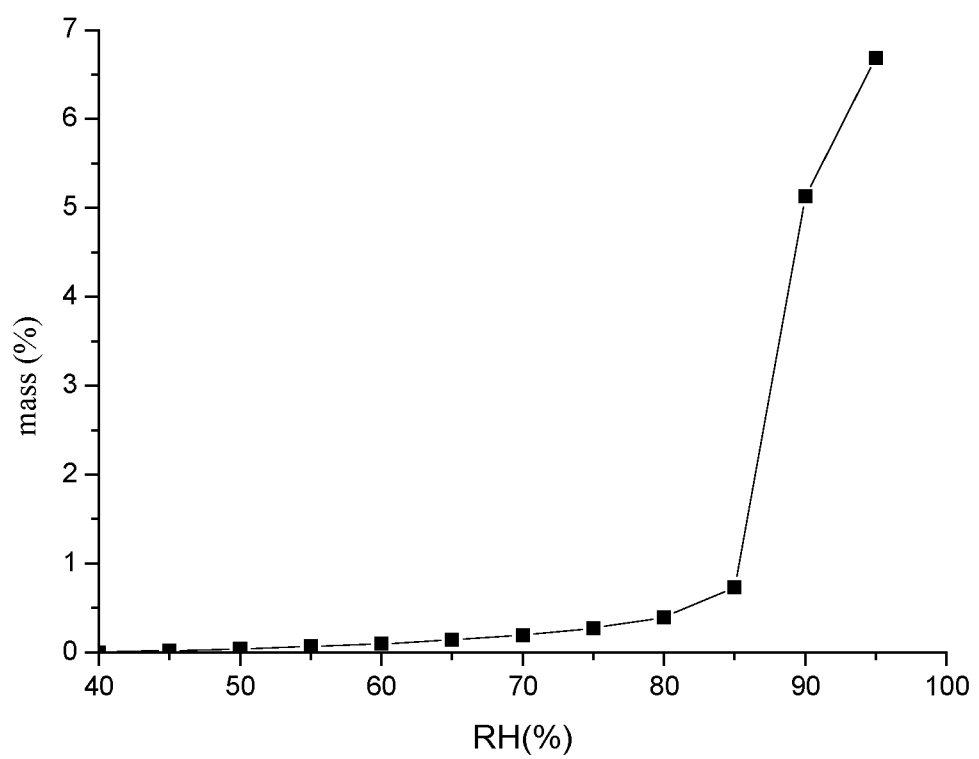
FIG. 5 is a hygroscopicity analysis (DVS) pattern of the PQQ crystal form B provided in Example 1.

A solid sample of the crystal form B of pyrroloquinoline quinone obtained in Example 1 was subjected to a hygroscopicity analysis. The analysis results were shown in FIG. 5, from which it can be seen that at a relative humidity of 85-95%, the crystal form adsorbed a molecule of water and was converted into a monohydrate compound, which had a low water absorption rate and increased slowly, which indicates that the crystal form had a low hygroscopicity.

The foregoing descriptions are merely preferred embodiments of the present invention, and not used to limit the present invention. Any modifications, equivalent replacements and improvements made within the spirit and principle of the present invention should be included in the protection scope of the present invention.

The invention claimed is:

1. A crystal form B of pyrroloquinoline quinone, wherein the crystal form B of pyrroloquinoline quinone has characteristic diffraction peaks selected from the following group consisting of: 11.10±0.2°, 20.16±0.2°, 22.57±0.2°, 26.14±0.2°, and 29.95±0.2°.

2. The crystal form B of pyrroloquinoline quinone of claim 1, wherein the crystal form B of pyrroloquinoline quinone has further 3 or more characteristic diffraction peaks selected from the following group consisting of: 15.69, 16.52, 17.32, 18.64, 19.40, 20.53, 21.77, 24.05, 24.36, 25.42, 27.05, 27.60, 28.15, 29.37, 32.06, 33.96, 35.62, 36.97, and 38.09±0.2°.

3. The crystal form B of pyrroloquinoline quinone of claim 1, wherein the X-ray powder diffraction pattern of the crystal form B of pyrroloquinoline quinone is essentially as shown in FIG. 1.

4. The crystal form B of pyrroloquinoline quinone of claim 1, wherein the thermogravimetric analysis pattern of the crystal form B has a decomposition temperature at 260° C.

5. The crystal form B of pyrroloquinoline quinone of claim 1, wherein the crystal form B is an anhydrous crystal form.

Figure 2:
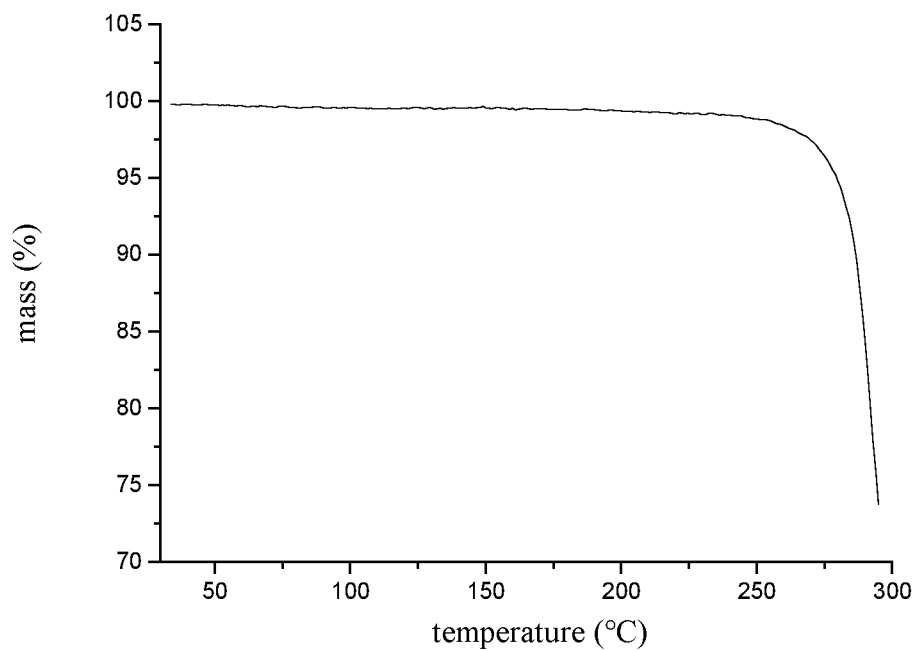
FIG. 2 is a thermogravimetric analysis (TG) pattern of the PQQ crystal form B provided in Example 1.

6. The crystal form B of pyrroloquinoline quinone of claim 1, wherein the thermogravimetric analysis pattern of the crystal form B of pyrroloquinoline quinone is essentially as shown in FIG. 2.

Figure 3:
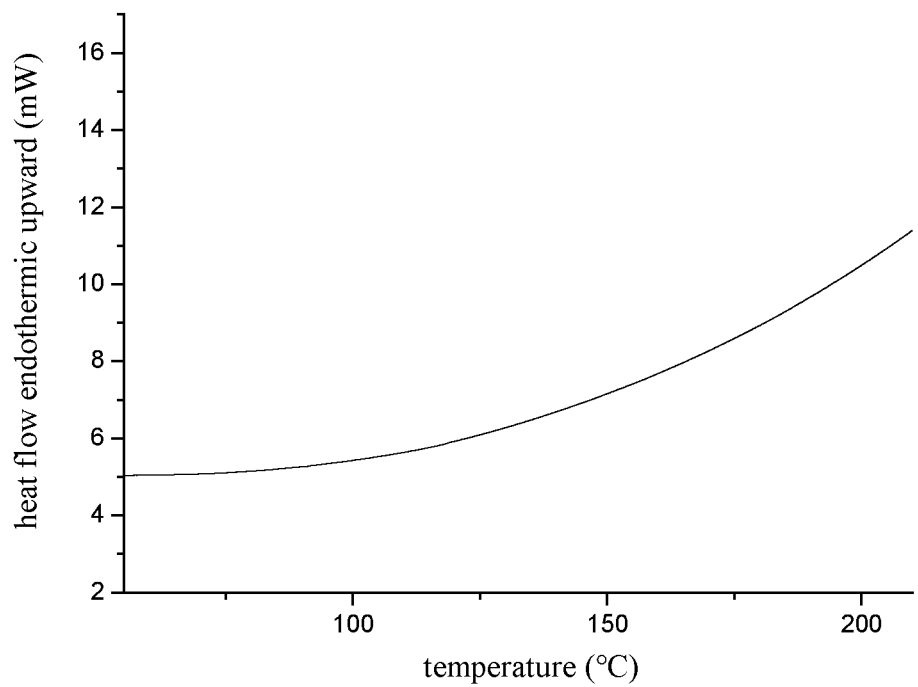
FIG. 3 is a differential scanning calorimetry (DSC) pattern of the PQQ crystal form B provided in Example 1.

7. The crystal form B of pyrroloquinoline quinone of claim 1, wherein the differential scanning calorimetry pattern of the crystal form B of pyrroloquinoline quinone is essentially as shown in FIG. 3.

8. The crystal form B of pyrroloquinoline quinone of claim 1, wherein the infrared spectrum of the crystal form B has characteristic peaks at least at 3344 $cm^{-1}$, 3257 $cm^{-1}$, 2808 $cm^{-1}$, 2596 $cm^{-1}$, 1745 $cm^{-1}$, 1726 $cm^{-1}$, 1710 $cm^{-1}$, 1691 $cm^{-1}$, 1643 $cm^{-1}$, 1508 $cm^{-1}$, 1402 $cm^{-1}$, 1336 $cm^{-1}$, 1261 $cm^{-1}$, 1207 $cm^{-1}$, 1080 $cm^{-1}$, and 769 $cm^{-1}$.

Figure 4:
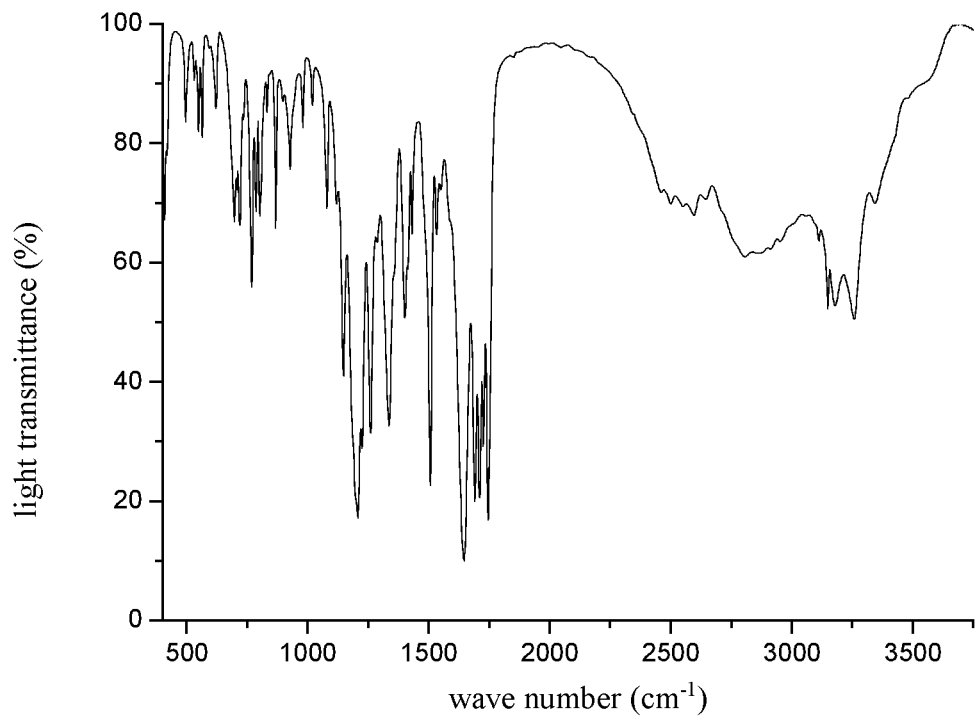
FIG. 4 is an infrared spectrum (IR) chart of the PQQ crystal form B provided in Example 1.

9. The crystal form B of pyrroloquinoline quinone of claim 1, wherein the infrared spectrum of the crystal form B of pyrroloquinoline quinone is essentially as shown in FIG. 4.

10. The crystal form B of pyrroloquinoline quinone of claim 1, wherein the hygroscopicity analysis of the crystal form B shows that one molecule of water at a relative humidity of 85-95% is adsorbed to form a monohydrate.

11. A method for preparing the crystal form B of pyrroloquinoline quinone of claim 1, comprising the steps of: pyrroquinoline quinine acid is placed in a vacuum drying oven at room temperature, and the temperature is raised, thereby obtaining the crystal form B of pyrroloquinoline quinone.

12. The method of claim 11, wherein the temperature is raised to 130-160° C.

13. The method of claim 11, wherein the time is kept for 3-5 hours after the temperature is raised.

* * * * *